United States Patent
Ono et al.

(10) Patent No.: US 7,192,747 B2
(45) Date of Patent: Mar. 20, 2007

(54) METHODS FOR PRODUCING L-AMINO ACIDS

(75) Inventors: Yukiko Ono, Kawasaki (JP); Hisashi Yasueda, Kawasaki (JP); Yoshio Kawahara, Kawasaki (JP); Shinichi Sugimoto, Kawasaki (JP)

(73) Assignee: Ajinomoto, Co. Inc., Tokyo (JP)

( * ) Notice: Subject to any disclaimer, the term of this patent is extended or adjusted under 35 U.S.C. 154(b) by 707 days.

(21) Appl. No.: 10/309,089

(22) Filed: Dec. 4, 2002

(65) Prior Publication Data

US 2003/0166174 A1 Sep. 4, 2003

Related U.S. Application Data

(63) Continuation of application No. 09/637,028, filed on Aug. 14, 2000, now abandoned.

(30) Foreign Application Priority Data

Aug. 17, 1999 (JP) ................. 11-230347

(51) Int. Cl.
*C12P 13/04* (2006.01)
*C12P 13/14* (2006.01)
*C12P 13/12* (2006.01)

(52) U.S. Cl. .............. 435/106; 435/110; 435/113

(58) Field of Classification Search ............... 435/106, 435/110, 113

See application file for complete search history.

(56) References Cited

U.S. PATENT DOCUMENTS 3,930,947 A 1/1976 Morinaga et al.

FOREIGN PATENT DOCUMENTS

| EP | 0 834 559 | 4/1965 |
| EP | 0 733 710 | 9/1996 |
| GB | 996 544 | 6/1965 |
| GB | 1 270 006 | 4/1972 |
| JP | 45-25273 | 8/1990 |
| WO | WO 95/16042 | 6/1995 |

OTHER PUBLICATIONS

R. Whittenbury et al. Journal of General Microbiology, 61, 205-218 (1970).*
Derwent Publications, AN 1995-135905, JP 07 059583, Mar. 7, 1995.

* cited by examiner

*Primary Examiner*—Christopher R Tate
*Assistant Examiner*—Randall Winston
(74) *Attorney, Agent, or Firm*—Shelly Guest Cermak; Cermak & Kenealy, LLP (57) ABSTRACT

A methane-utilizing microorganism capable of producing L-amino acid, for example, bacteria belonging to type I, type X or type II in the taxonomic categorization methane-utilizing bacteria such as *Methylomonas albus, Methylococcus capsulatus* and *Methylosinus trichosporium,* is cultivated in a culture medium in contact with gas containing methane which is the main source of carbon, to allow the L-amino acid to be produced and accumulated in the medium, and the L-amino acid is collected from the medium.

8 Claims, 1 Drawing Sheet

Fig. 1

METHODS FOR PRODUCING L-AMINO ACIDS

BACKGROUND OF THE INVENTION

1. Field of the Invention

The present invention relates to methods for producing L-amino acids by fermentation. L-amino acids are widely used for drugs, feed, foodstuffs and so forth.

2. Related Art

As methods for producing amino acids from saccharides as a carbon source by utilizing microorganisms, there are known a method utilizing microorganisms of the genus *Brevibacterium* (Japanese Patent Publication (Kokoku) No. 51-19186/1976), a method utilizing microorganisms of the genus *Escherichia* (Japanese Patent Application No. 7-516087/1995) and so forth. Further, as methods for producing amino acids from methanol as a carbon source by utilizing microorganisms, there are known a method utilizing microorganisms of the genus *Achromobacter*, *Pseudomonas* or the like (Japanese Patent Publication No. 45-25273/1970) and so forth.

So far, however, no method has been known for producing L-amino acids from methane as a carbon source by utilizing microorganisms.

SUMMARY OF THE INVENTION

An object of the present invention is to provide methods for producing L-amino acids, which are useful as drugs, feed, foodstuffs and so forth, by using methane as a main carbon source.

The inventors of the present invention found that methane-utilizing bacteria, in particular, those bacteria belonging to type I, type X or type II in the phylogenetic classification, can produce L-amino acids by utilizing methane as a main carbon source. Thus, the present invention was accomplished.

That is, the present invention provides the followings.

(1) A method for production of an L-amino acid, comprising the steps of: cultivating a methane-utilizing microorganism capable of producing L-amino acid in a culture medium which is in contact with gas containing methane which is the main source of carbon, to allow the L-amino acid to be produced and accumulated in the medium, and collecting the L-amino acid from the medium.

(2) A method according to (1), wherein the microorganism belongs to type I, type X or type II in the taxonomic categorization of methane-utilizing bacteria.

(3) A method according to (2), wherein the microorganism belonging to type I, type X or type II belongs to the genus *Methylomonas, Methylococcus* or *Methylosinus*, respectively.

(4) A method according to (1), wherein the L-amino acid is selected from the group consisting of L-aspartic acid, L-threonine, L-serine, L-glutamic acid, L-proline, L-glycine, L-alanine, L-cysteine, L-valine, L-methionine, L-isoleucine, L-leucine, L-tyrosine, L-phenylalanine, L-lysine, L-histidine, L-arginine and L-tryptophan.

(5) A method according to (1), wherein the methane-utilizing microorganism capable of producing L-amino acid is a wild type strain.

(6) A method according to (1), wherein the methane-utilizing microorganism capable of producing L-amino acid is resistant to an L-amino acid or an analog thereof.

(7) A method according to (6), wherein the L-amino acid is L-lysine and the analog thereof is S-(2-aminoethyl)-cysteine.

(8) A method according to (1), wherein the methane-utilizing microorganism capable of producing L-amino acid is a mutant strain or a recombinant strain in which activity of at least one enzyme involved in biosynthesis of L-amino acid is enhanced.

(9) A method according to (8), wherein the microorganism is a transformant strain which harbors a vector capable of encoding at least one enzyme involved in biosynthesis of L-amino acid.

(10) A method according to (8) or (9), wherein the enzyme involved in L-amino acid biosynthesis is one or more enzymes selected from the group consisting of mutant dihydrodipicolinate synthase which is desensitized to the feedback inhibition by L-lysine, mutatant aspartokinase which is desensitized to the feedback inhibition by L-lysine, dihydrodipicolinate reductase and diaminopimelate dehydrogenase.

(11) A mutant strain of a methane-utilizing microorganism capable of producing L-amino acid and resistant to the an L-amino acid or an analog thereof.

(12) A transformant of a mthane-utilizing microorganism capable of producing L-amino acid which harbors a vector capable of encoding at least one enzyme involved in biosynthesis of L-amino acid.

In the present invention, the "L-amino acid producing ability" means an ability of the microorganism used for the present invention to produce and accumulate an L-amino acid in a medium, when the microorganism is cultured in the medium.

According to the present invention, it is enabled to efficiently produce L-amino acids from methane, which is inexpensive raw material.

PREFERRED EMBODIMENTS OF THE INVENTION

Hereafter, the present invention will be explained in detail.

The microorganism used for the method for producing L-amino acid of present invention is a microorganism that has methane assimilating ability and L-amino acid producing ability.

The microorganism having methane assimilating ability is not particularly limited so long as it originally has L-amino acid producing ability or it can be imparted with L-amino acid producing ability. Specific examples of such a microorganism include those belonging to type I, type X or type II defined in the phylogenetic systematics of methane-utilizing microorganism. The nomenclatural classification of methane-utilizing bacteria is not currently considered well established, and they are roughly classified into three types on the basis of the main carbon assimilation pathway, arrangement of the intracytoplasmic membranes and autotrophic carbon dioxide fixation ability (Peter N. Green, "Taxonomy of Methylotrophic Bacteria" in Methane and Methanol Utilizers, Edited by J. Colin Murrell and Howard Dalton, p. 25–27, p. 48–49, Plenum Publishing Corporation, 233 Spring Street, New York, N.Y. 10013-1578, USA). The inventors of the present invention studied bacteria belonging to these three types, i.e., type I, type X and type II, and found that all of them were suitable for producing L-amino acids from methane. Therefore, the present invention is considered to be widely applicable to methane-utilizing bacteria. As methane-utilizing bacteria belonging to type I, type X or type II, there can be specifically mentioned bacteria belonging to the genera *Methylomonas, Methylococcus* and *Methylosinus*, respectively. More specifically, there can be mentioned *Methylomonas albus, Methylococcus capsulatus* and *Methylosinus trichosporium*.

The microorganism having methane assimilating ability may also be isolated from nature. In order to isolate microorganisms having methane assimilating ability from nature, a sample can be collected from water of river, lake, sea and so forth, mud, ground, rock, portions of organisms such as animals and plants, cadavers and excrement of organisms, air or the like, mixed with a liquid medium or plated on a solid medium, and cultured by using methane as a sole carbon source, and microorganisms that can grow can be selected.

The microorganism used for the present invention is such a methane-utilizing bacterium as mentioned above, and is a microorganism which has L-amino acid producing ability at the same time. The microorganism of the present invention may be a wild type strain which originally has L-amino acid producing ability, or may be a mutant strain obtained by breeding or recombinant strain, in which L-amino acid producing ability is enhanced or to which L-amino acid producing ability is imparted. As the L-amino acids for which the present invention can be used, there can be mentioned L-aspartic acid, L-threonine, L-serine, L-glutamic acid, L-proline, L-glycine, L-alanine, L-cysteine, L-valine, L-methionine, L-isoleucine, L-leucine, L-tyrosine, L-phenylalanine, L-lysine, L-histidine, L-arginine, L-tryptophan (hereafter, these may be abbreviated as, respectively in the above order, L-Asp, L-Thr, L-Ser, L-Glu, L-Pro, L-Gly, L-Ala, L-Cys, L-Val, L-Met, L-Ile, L-Leu, L-Tyr, L-Phe, L-Lys, L-His, L-Arg and L-Trp). The amino acid produced by the present invention may consist of a single kind of amino acid, or arbitrary two or more kinds of amino acids may be produced simultaneously.

In order to impart L-amino acid producing ability to a wild type strain of methane-utilizing bacterium, there can be used methods conventionally used for breeding of coryneform bacteria, bacteria belonging to the genus *Escherichia* etc., for example, for acquisition of auxotrophic mutant strains, L-amino acid analog resistant strains or metabolic regulation mutant strains, and creation of recombinant strains in which genes for enzymes of L-amino acid biosynthesis pathway are enhanced (see "Amino Acid Fermentation", the Japan Scientific Societies Press [Gakkai Shuppan Center], 1st Edition, published on May 30, 1986, pp. 77 to 100).

For example, L-lysine producing bacteria are bred as mutants exhibiting auxotrophy for L-homoserine or L-threonine and L-methionine (Japanese Patent Publication (Kokoku) Nos. 48-28078/1973 and 56-6499/1981), mutants exhibiting auxotrophy for inositol or acetic acid (Japanese Patent Laid-open (Kokai) Nos. 55-9784/1980 and 56-8692/1981), or mutants that are resistant to oxalysine, lysine hydroxamate, S-(2-aminoethyl)-cysteine, γ-methyllysine, α-chlorocaprolactam, DL-α-amino-ε-caprolactam, α-amino-lauryllactam, aspartic acid analogue, sulfa drug, quinoid or N-lauroylleucine.

Further, L-glutamic acid producing bacteria can be bred as mutants exhibiting auxotrophy for oleic acid or the like. L-Threonine producing bacteria can be bred as mutants resistant to α-amino-β-hydroxyvaleric acid. L-Homoserine producing bacteria can be bred as mutants exhibiting auxotrophy for L-threonine or mutant resistant to L-phenylalanine analogues. L-Phenylalanine producing bacteria can be bred as mutants exhibiting auxotrophy for L-tyrosine. L-Isoleucine producing bacteria can be bred as mutants exhibiting auxotrophy for L-leucine. L-Proline producing bacteria can be bred as mutants exhibiting auxotrophy for L-isoleucine.

The mutagenesis treatment for obtaining a mutant strain may be UV irradiation or a treatment with mutagen used for conventional mutagenesis treatment such as N-methyl-N'-nitro-N-nitrosoguanidine (NTG) and nitrous acid. A methane-utilizing bacterium that has L-amino acid producing ability can also be obtained by selecting a spontaneous mutant of a methane-utilizing bacterium.

A target mutant strain can be obtained by inoculating a methane-utilizing bacterium, mutagenized or not mutagenized, to a medium containing an L-amino acid or an analog thereof at a concentration at which a wild type strain cannot grow, and isolating a mutant strain which can grow on the medium.

Obtained mutant strains may include those having L-amino acid producing ability comparable to a parent strain or even reduced L-amino acid producing ability compared with the parent strains. Therefore, it is preferable to select strains having increased L-amino acid producing ability compared with the parent strains.

Now, methods for imparting or enhancing L-amino acid producing ability by enhancing the expression of gene(s) coding for enzyme(s) of an L-amino acid biosynthetic pathway will be exemplified below.

[L-Lysine]

L-lysine producing ability can be imparted by, for example, enhancing activities of dihydrodipicolinate synthase and aspartokinase, and by further enhancing activities of dihydrodipicolinate reductase and diaminopimelate dehydrogenase, if necessary.

Activities of dihydrodipicolinate synthase and aspartokinase in methane-utilizing bacteria can be enhanced by transforming a methane-utilizing bacterium through introduction of a recombinant DNA prepared by ligating a gene fragment coding for dihydrodipicolinate synthase and a gene fragment coding for aspartokinase with a vector that functions in Methane-utilizing bacteria, preferably a multiple copy type vector. As a result of the increase in the copy numbers of the gene coding for dihydrodipicolinate synthase and the gene coding for aspartokinase in cells of the transformant strain, activities of these enzymes are enhanced. Hereafter, dihydrodipicolinate synthase, aspartokinase, aspartokinase III, dihydrodipicolinate reductase and diaminopimelate dehydrogenase are also referred to with abbreviations of DDPS, AK, AKIII, DDPR and DDH, respectively.

As a microorganism providing genes that code for above enzymes, any microorganisms can be used so long as the genes express and activity of corresponding eznymes increase in methane-utilizing bacteria. Such microorganisms may be wild type strains or mutant strains derived therefrom. Specifically, examples of such microorganisms include *E. coli (Escherichia coli)* K-12 strain, *Brevibacterium lactofermentum* and so forth. Since nucleotide sequences have been revealed for a gene coding for DDPS (dapA, Richaud, F. et al., *J. Bacteriol.*, 297, (1986)), a gene coding for AKIII (lysC, Cassan, M., Parsot, C., Cohen, G. N. and Patte, J. C., *J. Biol. Chem.*, 261, 1052 (1986)), a gene coding for DDPR (dapB, Bouvier, J. et al., *J. Biol. Chem.*, 259, 14829 (1984)), which were derived from *Escherichia* bacteria, and a gene coding for DDH derived from *Corynebacterium glutamicum* (Ishino, S. et al., *Nucleic Acids Res.*, 15, and 3917 (1987)), these genes can be obtained by PCR using primers synthesized based on the nucleotide sequences of these genes and chromosome DNA of microorganism such as *E. coli* K-12, *Brevibacterium lactofermentum* ATCC13869 or the like as a template. As specific examples, dapA and lysC derived from *E. coli* will be explained below. However, genes used for the present invention are not limited to them.

It is preferred that DDPS and AK used for the present invention do not suffer feedback inhibition by L-lysine. It is known that wild-type DDPS derived from *E. coli* suffers feedback inhibition by L-lysine, and that wild-type AKIII derived from *E. coli* suffers suppression and feedback inhibition by L-lysine. Therefore, dapA and lysC to be introduced into methane-utilizing bacteria preferably code for DDPS and AKIII having a mutation that desensitizes the feedback inhibition by L-lysine. Hereafter, DDPS having a mutation that eliminates the feedback inhibition by L-lysine is also referred to as "mutant DDPS", and DNA coding for the mutant DDPS is also referred to as "mutant dapA" or "dapA*". AKIII derived from *E. coli* having a mutation that eliminates the feedback inhibition by L-lysine is also referred to as "mutant AKIII", and DNA coding for the mutant AKIII is also referred to as "mutant lysC".

According to the present invention, DDPS and AK are not necessarily required to be a mutant. It has been known that, for example, DDPS derived from *Corynebacterium* bacteria originally does not suffer feedback inhibition by L-lysine.

A nucleotide sequence of wild-type dapA derived from *E. coli* is exemplified in SEQ ID NO: 1. The amino acid sequence of wild-type DDPS encoded by the nucleotide sequence is exemplified in SEQ ID NO: 2.

DNA coding for mutant DDPS that does not suffer feedback inhibition by L-lysine includes DNA coding for DDPS having the amino acid sequence shown in SEQ ID NO: 2 wherein the 118-histidine residue is replaced with a tyrosine residue.

The plasmid used for gene cloning may be any plasmid so long as it can replicate in microorganisms such as *Escherichia* bacteria, and specifically include pBR322, pTWV228, pMW119, pUC19 and so forth.

The vector that functions in methane-utilizing bacteria is, for example, a plasmid that can autonomously replicate in methane-utilizing bacteria. Specifically, there can be mentioned RSF1010, which is a broad host range vector, and derivatives thereof, for example, pAYC32 (Chistorerdov, A. Y., Tsygankov, Y. D. *Plasmid*, 16, 161–167, (1986)), pMFY42 (*Gene*, 44, 53, (1990)), pRP301, pTB70 (Nature, 287, 396, (1980)), pRS, which is used in the examples hereinafter, and so forth.

In order to prepare a recombinant DNA by ligating dapA and/or lysC to a vector that functions in methane-utilizing bacteria, the vector is digested with a restriction enzyme that corresponds to the termini of DNA fragment containing dapA and/or lysC. Ligation is usually preformed by using ligase such as T4 DNA ligase. dapA and lysC may be individually incorporated into separate vectors or into a single vector.

As a plasmid containing a mutant dapA coding for mutant DDPS, a broad host range plasmid RSF24P is known (WO95/16042). *E. coli* JM109 strain transformed with this plasmid was designated as AJ12395, and deposited at National Institute of Bioscience and Human-Technology, Agency of Industrial Science and Technology, Ministry of International Trade and Industry (postal code 305–8566, 1–3 Higashi 1-chome, Tsukuba-shi, Ibaraki-ken, Japan) on Oct. 28, 1993 and received an accession number of FERM P-13935. Then, it was transferred to an international deposition based on Budapest Treaty on Nov. 1, 1994, and received an accession number of FERM BP-4858.

As a plasmid containing a mutant dapA coding for mutant DDPS and a mutant lysC coding for mutant AKIII, a broad host spectrum plasmid RSFD80 is known (WO95/16042). *E. coli* JM109 strain transformed with this plasmid was designated as AJ12396, and deposited at National Institute of Bioscience and Human-Technology, Agency of Industrial Science and Technology, Ministry of International Trade and Industry on Oct. 28, 1993 and received an accession number of FERM P-13936. Then, it was transferred to an international deposition based on Budapest Treaty on Nov. 1, 1994, and received an accession number of FERM BP-4859. RSF24P and RSFD80 can be obtained in a known manner from the AJ12395 and AJ12396 strains, respectively.

The mutant dapA contained in RSFD80 has a nucleotide sequence of wild-type dapA shown in SEQ ID NO: 1 including replacement of C at the nucleotide number 623 with T. The mutant DDPS encoded thereby has an amino acid sequence of SEQ ID NO: 2 including replacement of the 118-histidine residue with a tyrosine residue.

In order to introduce a recombinant DNA prepared as described -above into methane-utilizing bacteria, any method can be used so long as it provides sufficient transformation efficiency. For example, electroporation can be used (Canadian Journal of Microbiology, 43, 197 (1997)). Further, there can also be used a method comprising mixing *E. coli* S17-1 strain which harbors a recombinant vector and recipient bacteria (methane-utilizing bacteria), and allowing their conjugation on a filter placed on an agar plate to introduce the recombinant vector into the recipient bacteria (FEMS Microbiology Letters 41, p. 185–188 (1987)).

Transformants containing the recombinant vector can easily be identified by using the drug selectivity of the vector. Furthermore, the target transformant vector can also be introduced into recipient bacteria by the triparental conjugal transfer using *Escherichia coli* which harbors a self-transmissible plasmid, *Escherichia coli* which harbors the target recombinant vector and recipient bacteria (methane-utilizing bacteria) (Snyder, L and Champness, W., Molecular Genetics of Bacteria, ASM Press, Washington, D.C.).

Examples of the *Escherichia coli* which harbors a self-transmissible plasmid include *Escherichia coli* HB101/pRK2013 (Ditta, G., Stanfield, S., Corbin, D., and Helinski, D. R., *Proc. Natl. Acad. Sci. USA*, 77, 7347 (1980)).

DDPS activity and/or AK activity can also be enhanced by the presence of multiple copies of dapA and/or lysC on chromosome DNA of methane-utilizing bacteria. In order to introduce multiple copies of dapA and lysC into chromosome DNA of methane-utilizing bacteria, homologous recombination is performed by using, as a target, a sequence that is present on chromosome DNA of methane-utilizing bacteria in a multiple copy number. As a sequence present on chromosome DNA in a multiple copy number, a repetitive DNA or inverted repeats present at the end of a transposable element can be used. Alternatively, as disclosed in Japanese Patent Laid-open (Kokai) No. 2-109985/1990, multiple copies of dapA and/or lysC can be introduced into chromosome DNA by mounting them on a transposon to transfer them. In both of the methods, as a result of increased copy number of dapA and lysC in transformed strains, activities of DDPS and AK should be amplified.

Besides the above gene amplification, DDPS activity and/or AK activity can be amplified by replacing an expression control sequence such as promoters of dapA or lysC with stronger ones (Japanese Patent Laid-open (Kokai) No. 1-215280/1989). As such strong promoters, there are known, for example, lac promoter, trp promoter, trc promoter, tac promoter, $P_R$ promoter and $P_L$ promoter of lambda phage, tet promoter, amyE promoter, spac promoter and so forth. Substitution of these promoters enhances expression of dapA and/or lysC, and thus DDPS activity and/or AK activity are amplified. Enhancement of expression control sequences can be combined with increase of the copy numbers of dapA and/or lysC.

In order to prepare a recombinant DNA by ligating a gene fragment and a vector, the vector is digested with a restriction enzyme corresponding to the terminus of the gene fragment. Ligation is usually performed by ligase such as T4 DNA ligase. As methods for digestion, ligation and others of DNA, preparation of chromosome DNA, PCR, preparation of plasmid DNA, transformation, design of oligonucleotides used as primers and so forth, conventional methods well known to those skilled in the art can be used. Such methods are described in Sambrook, J., Fritsch, E. F., and Maniatis, T., "Molecular Cloning: A Laboratory Manual, 2nd Edition", Cold Spring Harbor Laboratory Press, (1989) and so forth.

In addition to the enhancement of DDPS and AK, other enzymes involved in the L-lysine biosynthesis may also be enhanced. Such enzymes include phosphoenolpyruvate carboxylase (Japanese Patent Laid-open (Kokai) No. 60-87788/1985), aspartate aminotransferase (Japanese Patent Publication (Kokoku) No. 6-102028/1994), diaminopimelate pathway enzymes such as DDPR, DDH, diaminopimelate decarboxylase (see WO96/40934), diaminopimelate epimerase and so forth, or aminoadipate pathway enzymes such as homoaconitate hydratase and so forth.

Further, the microorganisms of the present invention may have decreased activity of one or more enzymes that catalyze reaction(s) for generating compound(s) other than L-lysine by branching off from the biosynthetic pathway of L-lysine, or may be deficient in such an enzyme. Illustrative examples of the enzyme that catalyzes a reaction for generating a compound other than L-lysine by branching off from the biosynthetic pathway of L-lysine include homoserine dehydrogenase (see WO95/23864).

The aforementioned techniques for enhancing activities of enzymes involved in the L-lysine biosynthesis can be similarly used for other amino acids mentioned below.

[L-Glutamic Acid]

L-Glutamic acid producing ability can be imparted to methane-utilizing bacteria by, for example, introducing DNA that codes for any one of enzymes including glutamate dehydrogenase (Japanese Patent Laid-open (Kokai) 61-268185/1986), glutamine synthetase, glutamate synthase, isocitrate dehydrogenase (Japanese Patent Laid-open (Kokai) Nos. 62-166890/1987 and 63-214189/1988), aconitate hydratase (Japanese Patent Laid-open (Kokai) Nos. 62-294086/1987 and 63-119688/1988), citrate synthase (Japanese Patent Laid-open (Kokai) Nos. 62-201585/1987 and 63-119688/1988), phosphoenolpyruvate carboxylase (Japanese Patent Laid-open (Kokai) Nos. 60-87788/1985 and 62-55089/1987), pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase (Japanese Patent Laid-open (Kokai) No. 63-102692/1988), glucose phosphate isomerase, glutamate-oxoglutarate aminotransferase (WO99/07853) and so forth.

Further, the microorganism of the present invention may have decreased activity of an enzyme that catalyzes a reaction for generating a compound other than L-glutamic acid by branching off from the biosynthetic pathway of L-glutamic acid, or may be deficient in such an enzyme. Illustrative examples of the enzyme that catalyzes a reaction for generating a compound other than L-glutamic acid by branching off from the biosynthetic pathway of L-glutamic acid include α-ketoglutarate dehydrogenase (αKGDH), isocitrate lyase, phosphate acetyltransferase, acetate kinase, acetohydroxy acid synthase, acetolactate synthase, formate acetyltransferase, lactate dehydrogenase, glutamate decarboxylase, 1-pyrophosphate dehydrogenase and so forth.

[L-Threonine]

L-Threonine producing ability can be imparted or enhanced by, for example, transforming methane-utilizing bacteria using a recombinant plasmid containing a threonine operon (see Japanese Patent Laid-open (Kokai) Nos. 55-131397/1980, 59-31691/1984, 56-15696/1981 and International Patent Publication in Japanese (Kohyo) No. 3-501682/1991).

The production ability can also be imparted or enhanced by enhancing a threonine operon having a gene coding for aspartokinase whose feedback inhibition by L-threonine is desensitized (Japanese Patent Publication (Kokoku) No. 1-29559/1989), a gene coding for homoserine dehydrogenase (Japanese Patent Laid-open (Kokai) No. 60-012995/1985) or a gene coding for homoserine kinase and homoserine dehydrogenase (Japanese Patent Laid-open (Kokai) No. 61-195695/1986).

Further, L-threonine producing ability can be improved by introducing DNA coding for a mutant phosphoenolpyruvate carboxylase having a mutation for desensitizing feedback inhibition by aspartic acid.

[L-Valine]

L-Valine producing ability can be imparted by, for example, introducing an L-valine biosynthesis gene whose control mechanism has been substantially eliminated into methane-utilizing bacteria. There may also be introduced a mutation that substantially eliminates a control mechanism of an L-valine biosynthesis gene carried by a microorganism belonging to the genus *Escherichia*.

Examples of the L-valine biosynthesis gene include, for example, the ilvGMEDA operon of *E. coli*. Threonine deaminase encoded by an ilvA gene catalyzes the deamination reaction converting L-threonine into 2-ketobutyric acid, which is the rate-determining step of L-isoleucine biosynthesis. Therefore, in order to attain efficient progression of the L-valine synthesis reactions, it is preferable to use an operon that does not express threonine deaminase activity. Examples of the ilvGMEDA operon that does not express such threonine deaminase activity include an ilvGMEDA operon wherein a mutation for eliminating threonine deaminase activity is introduced into ilvA, an ilvGMEDA operon wherein ilvA is disrupted and an ilvGMED operon wherein ilvA is deleted.

Since the ilvGMEDA operon suffers expression control of operon (attenuation) by L-valine and/or L-isoleucine and/or L-leucine, the region required for the attenuation is preferably removed or mutated to eliminate the suppression of expression by L-valine to be produced.

An ilvGMEDA operon which does not express threonine deaminase activity and in which attenuation is eliminated as described above can be obtained by subjecting a wild-type ilvGMEDA operon to a mutagenesis treatment or modifying it by means of gene recombination techniques (see WO96/06926).

Escherichia coli strain B-3996 which harbors plasmid pVIC40 containing the threonine operon (WO90/04636, International Patent Publication in Japanese (Kohyo) No. 3-501682/1991) was deposited at the All-Union Scientific Centre of Antibiotis (VNIIA, Address: Nagatinskaya Street 3-a, Moscow 113105, Russian Federation) from Nov. 19, 1987 with a registration number of RIA 1867. This strain is also deposited at the Russian National Collection of Industrial Microorganisms (VKPM, Address: Dorozhny proezd.1, Moscow 113545, Russian Federation) with an accession number of B-3996.

[L-Leucine]

L-Leucine producing ability is imparted or enhanced by, for example, introducing, into methane-utilizing bacteria, an genes L-leucine biosynthesis gene whose control mechanism has been substantially eliminated, in addition to having the above characteristics required for the production of L-valine. It is also possible to introduce such a mutation that the control mechanism of an L-leucine biosynthesis gene should be substantially desensitized. Examples of such a gene include, for example, an leuA gene which provides an enzyme in which inhibition by L-leucine is substantially desensitized.

[L-Isoleucine]

L-Isoleucine producing ability can be imparted by, for example, introducing a thrABC operon containing a thrA gene coding for aspartokinase I/homoserine dehydrogenase I derived from E. coli wherein inhibition by L-threonine has been substantially desensitized and an ilvGMEDA operon which contains an ilvA gene coding for threonine deaminase wherein inhibition by L-isoleucine is substantially desensitized and whose region required for attenuation is removed (Japanese Patent Laid-open (Kokai) No. 8-47397/1996).

[Other Amino Acids]

Biosyntheses of L-tryptophan, L-phenylalanine, L-tyrosine, L-threonine and L-isoleucine can be enhanced by increasing phosphoenolpyruvate producing ability of methane-utilizing bacteria (WO97/08333).

The production abilities for L-phenylalanine and L-tyrosine are improved by enhancing a desensitized chorismate mutase-prephenate dehydratase (CM-PDT) gene (Japanese Patent Laid-open (Kokai) Nos. 5-236947/1993 and 62-130693/1987) and a desensitized DS (3-deoxy-D-arabinoheptulonate-7-phosphate synthase) gene (Japanese Patent Laid-open (Kokai) Nos. 5-236947/1993 and 61-124375/1986).

The producing ability of L-tryptophan is improved by enhancing a tryptophan operon containing a gene coding for desensitized anthranilate synthetase (Japanese Patent Laid-open (Kokai) Nos. 57-71397/1982, 62-244382/1987 and U.S. Pat. No. 4,371,614).

L-amino acids can be produced by cultivating methane-utilizing bacteria having L-amino acid producing ability obtained as described above in a medium in the presence of methane utilized as a main carbon source to produce and accumulate L-amino acids in the culture, and collecting the L-amino acids from the culture. The medium used for the present invention may be a natural or synthetic medium so long as it contains nitrogen source, inorganic ions and other trace amount organic components as required.

The culture may be performed by methods usually used for cultivating methane-utilizing bacteria.

As the main carbon source, methane is used. When the culture is performed in a closed system with shaking or as standing culture, for example, methane is injected into the culture vessel so that medium in the vessel is in contact with mixure of air and methane of which methane consists of 1–70%. When the culture is performed in an open system as aerobic culture, methane gas is bubbled into the medium to a concentration of 0.001–10 VVM.

As the nitrogen source, potassium nitrate, sodium nitrate, nitric acid, ammonia gas, aqueous ammonia, ammonium chloride, ammonium sulfate, ammonium nitrate, ammonium acetate, ammonium phosphate, urea and so forth are added to the medium in an amount of 0.01–10%. In addition to these, small amount of the components such as potassium phosphate, sodium phosphate, magnesium sulfate, calcium chloride, iron-EDTA, copper sulfate and so forth are usually added.

The culture is performed with shaking, or as standing culture or culture with babbling and stirring, and all of these cultures are performed under an aerobic condition. The culture is performed at a temperature of 15–80° C. and pH of the medium at pH 4–9, and it is usually completed within 16–200 hours.

Collection of L-amino acids from culture is attained by a combination of known methods such as those using ion exchange resin, precipitation and others.

EXAMPLES

Hereafter, the present invention will be further specifically explained with reference to the following examples.

Example 1

Acquisition of L-amino Acid Producing Strain Derived from Methylomonas albus (1) Acquisition of L-lysine Resistant Strain of Methylomonas albus The NCIMB 11123 strain, a wild type strain of Methylomonas albus, was cultured at 30° C. for 48 hours in NMS medium mentioned below in the presence of methane, and the obtained bacterial cells were subjected to mutagenesis treatment with NTG in a conventional manner (NTG 50 μg/ml, 30° C., 30 minutes). The NCIMB 11123 strain can be obtained from The National Collections of Industrial and Marine Bacteria Ltd. (Address: NCIMB Lts., Torry Research Station 135 Abbey Road, Aberdeen AB98DG, United Kingdom).

[Composition of NMS Medium]

Potassium nitrate: 1 g/L, magnesium sulfate: 1 g/L, calcium chloride: 0.2 g/L, iron-EDTA: 3.8 mg/L, sodium molybdate: 0.26 mg/L, copper sulfate: 0.2 mg/L, iron sulfate: 0.5 mg/L, zinc sulfate: 0.4 mg/L boric acid: 0.015 mg/L, cobalt chloride: 0.05 mg/L, sodium EDTA: 0.25 mg/L, manganese chloride: 0.02 mg/L, nickel chloride: 0.01 mg/L, disodium phosphate 0.716 g/L, potassium phosphate: 0.26 g/L (pH 6.8)

The aforementioned cells subjected to the mutagenesis treatment were plated on NMS agar medium containing 10 mM of L-lysine, and cultured at 30° C. for 3–40 days while 50% of methane was added to the gaseous phase which was in contact with the medium (henceforth referred to as "in the presence of 50% methane"). The emerged colonies were isolated, inoculated to NMS agar medium, and cultured at 30° C. for 3–30 days in the presence of 50% methane. 1/10 platinum loop of cells of the lysine resistant strain obtained as described above were inoculated to 3 ml of NMS medium in 30-ml volume pressure-proof test tube and 15 ml of methane was injected into each tube and cultured at 30° C. for 14 days with shaking.

After the culture was completed, the cells were removed by centrifugation and amino acids contained in the obtained culture supernatant was analyzed by an amino acid analyzer (Hitachi L-8500). A strain that exhibited increased accumulated amounts of, in particular, L-valine and L-leucine was selected, and designated as No. 107-4 strain. The No. 107-4 strain was given with a private number of AJ13630, and deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Aug. 6, 1999 with an accession number of FERM P-17507, and transferred from the original deposit to international deposit based on Budapest Treaty on Jul. 27, 2000, and has been deposited as an accession number of FERM BP-7250.

(2) Acquisition of AEC Resistant Strain Derived From *Methylomonas albus*

An AEC resistant strain was obtained from the wild type strain of *Methylomonas albus* in the same manner as in (1) except that 1, 3 or 4.5 mM of AEC was used instead of 10 mM of L-lysine. The obtained 74 AEC resistant strains were each cultured in a test tube in the same manner as the above (1). Distribution of L-lysine accumulation of these strains is shown in Table 1.

TABLE 1

Distribution of L-lysine accumulation of AEC resistant strains derived from *Methylomonas albus*

| Strain | L-Lys (mg/L) | | |
|---|---|---|---|
| | 0 | –0.50 | –1.00 |
| Wild type strain | 1 | 0 | 0 |
| 1 mM AEC resistant strain | 34 | 2 | 0 |
| 3 mM AEC resistant strain | 2 | 16 | 16 |
| 4.5 mM AEC resistant strain | 0 | 1 | 1 |

Although accumulation of L-lysine was not observed for the wild type strain, accumulation of L-lysine was observed for two strains of the 1 mM AEC resistant strains among 36 strains. Accumulation of lysine was observed for 32 strains of 3 mM AEC resistant strains out of 34 strains, and 16 strains among them showed accumulation of L-lysine higher than 0.50 mg/L. As for the 4.5 mM AEC resistant strains, accumulation of lysine was observed for both of the two strains, and one strain showed accumulation of L-lysine higher than 0.50 mg/L. Among these AEC resistant strains, the strain that exhibited the highest L-lysine accumulation was designated as No. 135-3-63 strain. The No. 135-3-63 strain was given with a private number of AJ13631, and deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Aug. 6, 1999 as an accession number of FERM P-17508, and transferred from the original deposit to international deposit based on Budapest Treaty on Jul. 27, 2000, and has been deposited as an accession number of FERM BP-7251.

Example 2

Production of L-amino Acids Using L-lysine Resistant Strain of *Methylomonas albus*

A wild type strain and the No.107-4 strain of *Methylomonas albus* were each inoculated in an amount of 2 platinum loops to NMS medium containing 1.5% of agar, and cultured at 30° C. for 7 days in the presence of 50% methane. The whole amount of the obtained cells were inoculated to 500 ml of AMS medium supplemented with 4 μM $CuSO_4$ contained in a 1-L volume fermentation vessel (produced by Biott), and cultured at 30° C. under the conditions of stirring at 400 rpm or above, dissolved oxygen concentration of not less than 5 ppm, with supply of air and methane at 200 ml/minute and 100 ml/minute, respectively. AMS medium is a medium that is identical to NMS medium except that $KNO_3$ is replaced with an equivalent amount of $NH_4Cl$ in terms of nitrogen. During the culture, pH of the medium was automatically controlled to be 6.5 with ammonia gas. 10 ml of 1 mM $CuSOs_4$ was added 39 hours and 65 hours after the culture was started.

After the culture was completed, the cells were removed by centrifugation and amino acids contained in the obtained culture supernatant were analyzed by an amino acid analyzer. The results are shown in Table 2. L-Amino acids contained in the culture supernatant of the No. 107-4 strain were increased by 13 times for L-Val, 4 times for L-Leu, 3 times for L-Tyr, 2 times for L-Phe and 1.7 times for L-Ile, compared with the wild type strain. Further, although L-Lys was not detected for the wild type strain, 3.9 mg/L of L-Lys was accumulated by the No. 107-4 strain.

TABLE 2

Amino acid accumulation by L-lysine resistant strain derived from *Methylomonas albus*

| | Amino acid accumulation by L-lysine resistant strain L-amino acid (mg/L) | |
|---|---|---|
| | Wild type strain | 107-4 |
| L-Thr | 6.2 | 8.8 |
| L-Glu | 79.2 | 102.8 |
| L-Ala | 25.8 | 25.6 |
| L-Val | 25.0 | 330.3 |
| L-Ile | 15.6 | 27.2 |
| L-Leu | 55.9 | 250.4 |
| L-Tyr | 7.2 | 23.9 |
| L-Phe | 24.0 | 56.6 |
| L-Lys | 0.0 | 3.9 |
| L-His | 2.7 | 3.5 |
| L-Arg | 1.0 | 1.3 |

Example 3

Production of L-lysine Utilizing AEC Resistant Strain of *Methylomonas albus*

A wild type strain of *Methylomonas albus* and the AEC resistant strain No. 135-3-63 were inoculated each in an amount of one colony to NMS medium containing 1.5% of agar, and cultured at 30° C. for 7 days in the presence of 50% methane. 1/10 Platinum loop of each of the obtained seed culture was inoculated to 3 ml of NMS medium in a 30-ml volume pressure-proof test tube and 15 ml of methane was injected and cultured at 30° C. for 72 hours with shaking. After the culture was completed, the cells were removed by centrifugation and amino acids contained in the obtained culture supernatant was analyzed by an amino acid analyzer. The results are shown in Table 3. While L-Lys was not detected in the culture supernatant of the wild type strain, 0.86 mg/L of L-Lys was accumulated by the No.135-3-63 strain.

TABLE 3

L-lysine accumulation by AEC resistant strain derived from *Methylomonas albus*

| Strain | L-Lys (mg/L) |
| --- | --- |
| Wild type strain | 0.00 |
| No. 135-3-63 | 0.86 |

Example 4

Acquisition of AEC Resistant Strain Derived From *Methylococcus capsulatus* Bath The NCIMB 11132 strain, a wild type strain of *Methylococcus capsulatus* Bath, was cultured at 37° C. for 48 hours in NMS medium in the presense of methane, and the obtained bacterial cells were subjected to mutagenesis treatment with NTG in a conventional manner (NTG 25 μg/ml, 30° C., 30 minutes). The NCIMB 11132 strain can be obtained from The National Collections of Industrial and Marine Bacteria Ltd. (Address: NCIMB Lts., Torry Research Station 135 Abbey Road, Aberdeen AB98DG, United Kingdom).

The aforementioned cells subjected to the mutagenesis treatment were plated on NMS agar medium containing 3 mM of AEC, and cultured at 37° C. for 3–30 days in the presence of 50% methane. The emerged colonies were isolated, inoculated to NMS agar medium, and cultured at 37° C. for 3–30 days in the presence of 50% methane. ¹⁄₁₀ Platinum loop of the AEC resistant strain obtained as described above was inoculated to 3 ml of NMS medium in a 30-ml volume pressure-proof test tube and 15 ml of methane was injected and cultured at 37° C. for 3 days with shaking.

After the culture was completed, the cells were removed by centrifugation and amino acids contained in the obtained culture supernatant were analyzed by an amino acid analyzer (Hitachi L-8500). Strains that exhibited increased accumulated amounts of L-amino acids compared with the wild type strain as the parent strain were selected, and designated as No. 167-22 strain and No. 167-87 strain. The No. 167-22 strain was given with a private number of AJ13618, and deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Aug. 6, 1999 as an accession number of FERM P-17506 and transferred from the original deposit to international deposit based on Budapest Treaty on Jul. 27, 2000, and has been deposited as deposition number of FERM BP-7249.

Example 5

Production of L-amino Acids Utilizing AEC Resistant Strain of *Methylococcus capsulatus* Bath A wild type strain and the AEC resistant strains No. 167-22 and No. 167-87 of *Methylococcus capsulatus* Bath were inoculated each in an amount of one colony to NMS medium containing 1.5% of agar, and cultured at 37° C. for 7 days in the presence of 50% methane. ¹⁄₁₀ Platinum loop of each obtained seed culture was inoculated to 3 ml of NMS medium in a 30-ml volume pressure-proof test tube and 15 ml of methane was injected and cultured at 37° C. for 72 hours with shaking. After the culture was completed, the cells were removed by centrifugation and amino acids contained in the obtained culture supernatant were analyzed by an amino acid analyzer. The results are shown in Table 4.

As for the No. 167-22 strain, L-amino acids contained in the culture supernatant were increased by 2 times for L-Asp, 2 times for L-Thr, 3 times for L-Ser, 2 times for L-Glu, 10 times for L-Val, 17 times for L-Ile, 69 times for L-Leu, 2 times for L-Tyr and 13 times for L-Phe, compared with the wild type strain. As for the No. 167-87 strain, L-amino acids contained in the culture supernatant were increased by 6 times for L-Asp, 3 times for L-Thr, 4 times for L-Ser, 3 times for L-Glu, 3 times for L-Ile, 7 times for L-Leu, 4 times for L-Phe, 2 times for L-Lys, 2 times for L-His and 4 times for L-Arg, compared with the wild type strain. Further, although L-Ala was not detected for the wild type strain, 1.73 mg/L and 1.74 mg/L of L-Ala was accumulated by the No. 167-22 strain and No. 167-87 strain, respectively.

TABLE 4

Amino acid accumulation by wild type strain and AEC resistant strains of *Methylococcus capsulatus* Bath

| | L-amino acid (mg/L) | | |
| --- | --- | --- | --- |
| | Wild type strain | No. 167-22 | No. 167-87 |
| L-Asp | 0.22 | 0.56 | 1.33 |
| L-Thr | 0.52 | 1.25 | 1.97 |
| L-Ser | 0.17 | 0.57 | 0.82 |
| L-Glu | 2.47 | 7.03 | 9.65 |
| L-Gly | 0.78 | —* | 1.51 |
| L-Ala | 0.00 | 1.73 | 1.74 |
| L-Val | 1.60 | 17.07 | 3.13 |
| L-Met | 0.98 | — | 1.61 |
| L-Ile | 0.29 | 5.10 | 1.12 |
| L-Leu | 0.28 | 19.56 | 1.99 |
| L-Tyr | 0.96 | 2.01 | 1.85 |
| L-Phe | 0.54 | 7.14 | 2.64 |
| L-Lys | 0.46 | — | 1.33 |
| L-His | 0.55 | — | 1.10 |
| L-Arg | 0.42 | — | 1.76 |

*: n.d. (no data)

Example 6

Acquisition of AEC Resistant Strain Derived From *Methylosinus trichosporium* OB3b Strain The NCIMB 11131 strain, a wild type strain of *Methylosinus trichosporium* OB3b, was cultured at 30° C. for 48 hours in NMS medium in the presense of methane, and the obtained bacterial cells were subjected to mutagenesis treatment with NTG in a conventional manner (NTG 30 µg/ml, 30° C., 30 minutes).

The NCIMB 11131 strain can be obtained from The National Collections of Industrial and Marine Bacteria Ltd. (Address: NCIMB Lts., Torry Research Station 135 Abbey Road, Aberdeen AB98DG, United Kingdom).

The aforementioned cells subjected to the mutagenesis treatment were plated on NMS agar medium containing 3 mM of AEC, and cultured at 37° C. for 7–30 days in the presence of 50% methane. The emerged colonies were isolated, inoculated to NMS agar medium, and cultured for at 37° C. for 7–30 days in the presence of 50% methane. 1/10 Platinum loop of the AEC resistant strain obtained as described above was inoculated to 3 ml of NMS medium in a 30-ml volume pressure-proof test tube and 15 ml of methane was injected and cultured at 30° C. for 5 days with shaking.

After the culture was completed, the cells were removed by centrifugation and amino acids contained in the obtained culture supernatant was analyzed by an amino acid analyzer (Hitachi L-8500). Strains that exhibited increased accumulated amounts of L-amino acids compared with the wild type strain were selected, and designated as No. 171-15 strain and No. 171-35 strain. The No. 171-15 strain was given with a private number of AJ13677, and deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on May 15, 2000 as an international deposition and received an accession number of FERM BP-7159.

Example 7

Production of L-amino Acids Using AEC Resistant Strains of *Methylosinus trichosporium* OB3b Strain A wild type strain, and the AEC resistant strains No. 171-15 and No. 171-35 of *Methylosinus trichosporium* OB3b were each inoculated in an amount of one colony to NMS medium containing 1.5% of agar, and cultured at 37° C. for 14 days in the presence of 50% methane. 1/10 Platinum loop of each obtained seed culture was inoculated to 3 ml of NMS medium in a 30-ml volume pressure-proof test tube and 15 ml of of methane was injected and cultured at 30° C. for 120 hours with shaking. After the culture was completed, the cells were removed by centrifugation and amino acids contained in the obtained culture supernatant was analyzed by an amino acid analyzer. The results are shown in Table 5.

As for the No. 171-15 strain, L-amino acids contained in the culture supernatant were increased by 3 times for L-Thr, 3 times for L-Ala, 10 times for L-Val, 3 times for L-Ile, 11 times for L-Leu and 3 times for L-Phe, compared with the wild type strain. As for the No. 171-35 strain, L-amino acids contained in the culture supernatant were increased by 2 times for L-Ala, 39 times for L-Leu and 2 times for L-Phe, compared with the wild type strain. Further, although L-Lys was not detected for the wild type strain, 0.19 mg/L and 0.27 mg/L of L-Lys was accumulated by the No. 171-15 strain and No. 171-35 strain, respectively.

TABLE 5

Amino acid accumulation by wild type strain and AEC resistant strains of *Methylosinus trichosporium* OB3b

| | L-amino acid (mg/L) | | |
|---|---|---|---|
| | Wild type strain | No. 171-15 | No. 171-35 |
| L-Thr | 0.29 | 0.93 | 0.50 |
| L-Gly | 0.32 | 0.59 | 0.46 |
| L-Ala | 0.80 | 3.01 | 1.70 |
| L-Val | 1.01 | 10.02 | 1.35 |
| L-Ile | 0.67 | 2.03 | 0.97 |
| L-Leu | 0.60 | 6.98 | 23.47 |
| L-Tyr | 0.62 | 0.84 | 0.95 |
| L-Phe | 0.70 | 2.58 | 1.46 |
| L-Lys | 0.00 | 0.19 | 0.27 |

Example 8

Figure 1:
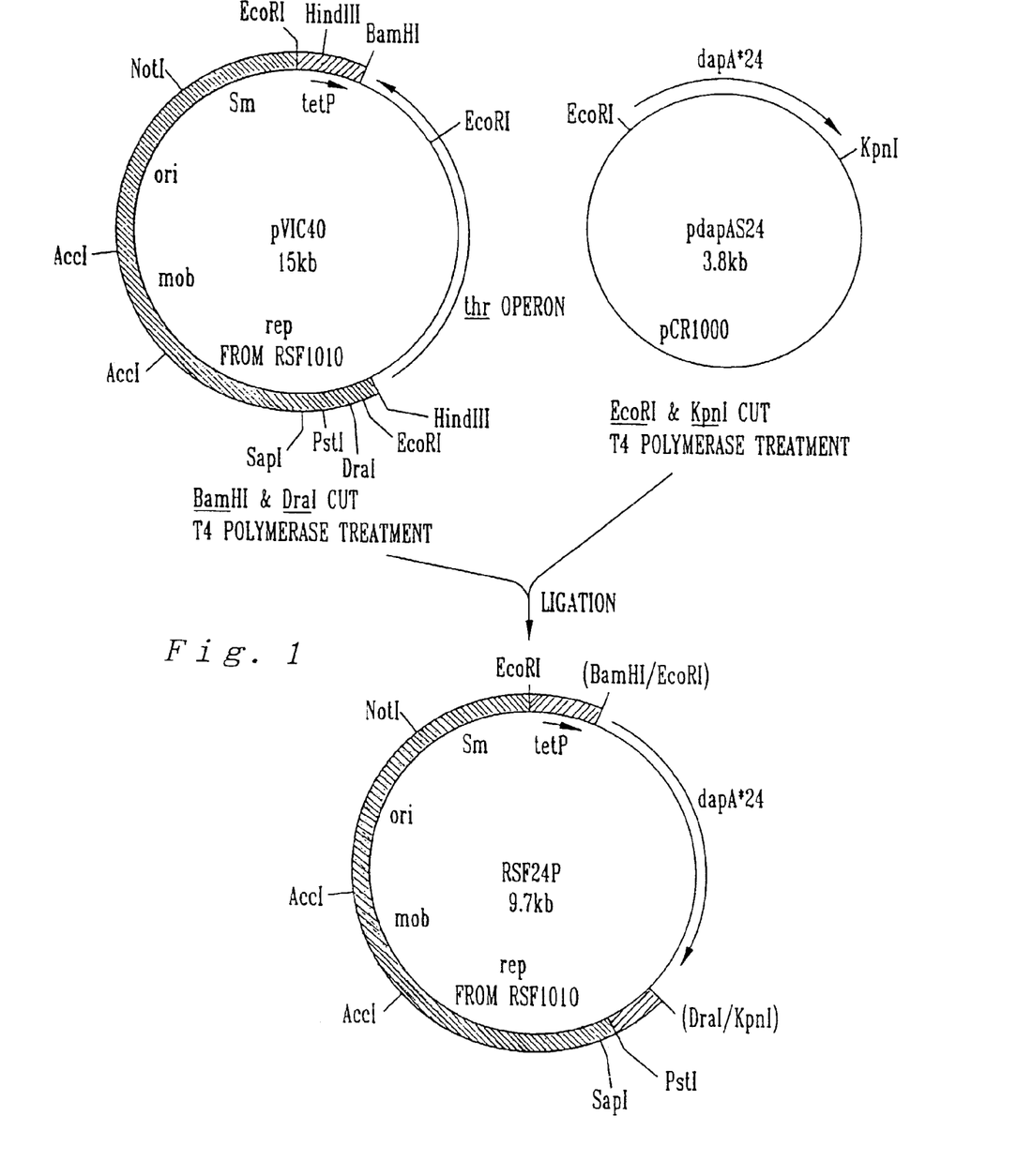
FIG. 1 shows the construction process of the plasmid RSF24P which has a mutant dapA. "dapA*24" represents a mutant dapA which codes for a mutant DDPS in which the 118th histidine residue was replaced with a tyrosine residue.

Introduction of dapA* Into Wild Type Strains of *Methylomonas albus* and *Methylococcus capsulatus* Bath In order to introduce dapA* into *Methylomonas albus* or *Methylococcus capsulatus* Bath strain, plasmid RSF24P was used. This plasmid contains DNA (dapA*) coding for mutant dihydrodipicolinate synthase (DDPS) of *Escherichia coli* desensitized to the feedback inhibition by L-lysine, which was disclosed in WO95/16042. RSF24P is a plasmid which was constructed by inserting dapA*, which coded for a mutant DDPS in which the 118th histidine residue was replaced by a tyrosine residue, into the plasmid pVIC40 containing the threonine operon (WO90/04636, International Patent Publication in Japanese (Kohyo) No. 3-501682/1991) at a site downstream of the promoter for the tetracycline resistance gene (see FIG. 1). The threonine operon was deleted from pVIC40 during the process of the insertion of dapA*.

The *Escherichia coli* JM109 strain harboring the RSF24P plasmid was designated as AJ12395, and deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 28, 1993 and received an accession number of FERM P-13935. Then, it was transferred to an international deposition based on Budapest Treaty on Nov. 1, 1994, and received an accession number of FERM BP-4858.

As a control, plasmid pRS (WO90/04636, International Patent Publication in Japanese (Kohyo) No. 3-501682/1991) was used. This plasmid was produced by deleting the DNA region coding for the threonine operon from the pVIC40 plasmid and hence had only the vector region. pRS was produced as follows. pVIC40 was digested with EcoRI to remove a fragment of about 6.5 kb containing the threonine operon. The promoter for the streptomycin resistance gene was deleted by this operation and hence expression of the gene became unstable. Therefore, promoter of a threonine operon whose attenuator had been removed was inserted into the EcoRI site of the above digested plasmid in the correct direction with respect to the streptomycin resistance gene. A 224 bps fragment containing the threonine operon promoter was prepared in a conventional manner by PCR using the following oligonucleotides PT-4 and PT-5 as primers and pVIC40 as template. The 224 bps fragment was digested with EcoRI and MunI and ligated to pVIC40 digested with EcoRI to introduce the threonine operon promoter into the plasmid. *Escherichia coli* JM109 was transformed with the obtained plasmid, and PCR was performed for each transformant strain by using PT-4 and the following primer SM-1. A transformant for which a band was detected at about 270 bps was selected as one in which the promoter was inserted in collect direction with respect to the streptomycin resistance gene.

```
[Primers]
PT-4:
GCGCGAATTCCAACGGGCAATATGTCTCTG  (SEQ ID NO: 3)

PT-5:
GCGCCAATTGGATGTACCGCCGAACTTCAA  (SEQ ID NO: 4)

SM-1:
CAGTTTTCTGATGAAGCGCG            (SEQ ID NO: 5)
``` pRS and RSF24P obtained as described above were each introduced into *Escherichia coli* S17-1 in a conventional manner to obtain S17-1/pRS and S17-1/RSF24P, respectively.

Each of S17-1/pRS and S17-1/RSF24P was inoculated into 3 ml of LB medium containing 20 μg/L of streptomycin in a 30-ml volume test tube, and cultured at 37° C. for 18 hours with shaking. On the other hand, wild type strains of *Methylomonas albus* and *Methylococcus capsulatus* Bath were each inoculated to 3 ml of NMS media contained in a 30-ml volume pressure-proof test tube, in which 15 ml of methane was then enclosed, and cultured at 30° C. for *Methylomonas albus* or at 37° C. for *Methylococcus capsulatus* Bath strain for two days with shaking.

0.1 ml of the culture bloth of donor strain (S17-1/pRS or S17-1/RSF24P) and 1.4 ml of the culture bloth of recipient strain (*Methylomonas albus* and *Methylococcus capsulatus* Bath strain) were mixed in a 1.5 ml-volume microtube, and centrifuged to remove the supernatant. The pellet of the cells obtained for each case was subjected to heat shock at 50° C. for 1 minute, then suspended in a small amount of NMS medium and transferred onto a membrane filter. This membrane filter was placed on NMS medium containing 1.5% of agar, and left stand at 30° C. for *Methylomonas albus* or at 37° C. for *Methylococcus capsulatus* Bath. Four hours later, the membrane filter was washed with a small amount of NMS medium, and the cells were collected into a microtube. These cells were plated on NMS medium containing 10 μg/ml of streptomycin and 1.5% of agar, and cultured at 30° C. for *Methylomonas albus* or at 37° C. for *Methylococcus capsulatus* Bath for 3–14 days. The emerged colonies were inoculated into 3 ml of NMS medium containing 10 μg/L of streptomycin in a 30-ml volume pressure-proof test tube, in which 15 ml of methane was then enclosed, and cultured at 30° C. for *Methylomonas albus* or at 37° C. for *Methylococcus capsulatus* Bath for 10 days with shaking.

After the culture was completed, the cells were separated from the culture by centrifugation, and the presence of each plasmid was confirmed in a conventional manner. Hereafter, *Methylomonas albus* strains which harbor each of pRS and RSF24P are referred to as *Methylomonas albus*/pRS and *Methylomonas albus*/RSF24P, respectively. *Methylococcus capsulatus* Bath strains which harbor each of pRS and RSF24P are referred to as *Methylococcus capsulatus* Bath/pRS and *Methylococcus capsulatus* Bath/RSF24P, respectively.

Example 9

Effect of dapA* Gene Amplification in *Methylomonas albus*

A wild type strain of *Methylomonas albus*, *Methylomonas albus*/pRS (comprising only the vector) and *Methylomonas albus*/RSF24P (comprising dapA*) were cultured in the same manner as in Example 3 except that NMS medium containing 10 μg/ml of streptomycin was used instead of NMS medium for the strains harboring the plasmids, and the amino acid contained in each culture supernatant were quantified. The results are shown in Table 6. Increase in L-Lys accumulation was observed in the dapA* amplified strain.

TABLE 6

Effect of dapA* gene amplification in *Methylomonas albus*

| Strain | L-Lys accumulation (mg/L) |
| --- | --- |
| *Methylomonas albus* | 0.00 |
| *Methylomonas albus*/pRS | 0.00 |
| *Methylomonas albus*/RSF24p | 0.48 |

Example 10

Effect of dapA* Gene Amplification in *Methylococcus capsulatus* Bath

A wild type strain of *Methylococcus capsulatus* Bath, *Methylococcus capsulatus* Bath/pRS (comprising only the vector) and *Methylococcus capsulatus* Bath/RSF24P (comprising dapA*) were cultured in the same manner as in Example 9 except that they were cultured at 37° C. instead of at 30° C., and the amino acid contained in each culture supernatant were quantified. The results are shown in Table 7. Increase in L-Lys accumulation was observed in the dapA* amplified strain.

TABLE 7

Effect of dapA* amplification in *Methylococcus capsulatus* Bath

| Strain | L-Lys accumulation (mg/L) |
| --- | --- |
| *Methylococcus capsulatus* Bath | 0.23 |
| *Methylococcus capsulatus* Bath/pRS | 0.25 |
| *Methylococcus capsulatus* Bath/RSF24p | 3.07 |

Example 11

Production of L-amino Acids Utilizing *Methylococcus capsulatus* Bath

A wild type strain of *Methylococcus capsulatus* Bath, *Methylococcus capsulatus* Bath/pRS and *Methylococcus capsulatus* Bath/RSF24P were cultured in the same manner as in Example 2 except that they were cultured at 37° C. instead of at 30° C. 10 μg/ml of streptomycin was added to the medium for cultivating the strains harboring the plasmids. Further, 10 ml of 1 mM $CuSO_4$ was added 19 hours and 65 hours after the start of the culture.

After the culture was completed, the cells were separated by centrifugation and amino acids contained in the obtained culture supernatant was analyzed by an amino acid analyzer. The results are shown in Table 8. *Methylococcus capsulatus* Bath/RSF24P accumulated 223 mg/L of L-Lys. The wild type strain of *Methylococcus capsulatus* Bath and *Methylococcus capsulatus* Bath/pRS accumulated 122 mg/L and 220 mg/L of L-Glu, respectively.

TABLE 8

Amino acid accumulation of wild type strain and
dapA* amplified strain of *Methylococcus capsulatus* Bath

| | L-amino acid (mg/L) | | |
|---|---|---|---|
| | Wild type strain | /pRS | /RSF24P |
| L-Glu | 122.8 | 220.9 | 32.9 |
| L-Lys | 10.6 | 23.3 | 223.6 |

Example 12

Introduction of dapA*, lysC*, dapB and ddh Into Wild Type Strain of *Methylococcus capsulatus* Bath For introduction of dapA*, lysC*, dapB and ddh into a wild type strain of *Methylococcus capsulatus* Bath, there was used plasmid pCABD2, which was disclosed in WO95/16042, containing DNA which coded for dihydrodipicolinate synthase (DDPS) of *Escherichia coli* having a mutation for desensitizing the feedback inhibition by L-lysine (dapA*24), DNA which coded for aspartokinase III of *Escherichia coli* having a mutation for desensitizing the feedback inhibition by L-lysine (lysC*80), DNA which coded for dihydrodipicolinate reductase of *Escherichia coli* (dapB) and DNA which coded for diaminopimelate dehydrogenase of *Brevibacterium lactofermentum* (ddh).

The aforementioned pCABD2 was introduced into *Escherichia coli* JM109 in a conventional manner to obtain JM109/pCABD2.

JM109/pCABD2 was inoculated into 3 ml of LB medium containing 20 μg/L of streptomycin, which was contained in a 30-ml volume test tube, and cultured at 37° C. for 18 hours with shaking. The *Escherichia coli* HB101/pRK2013 disclosed in reference (Ditta, G., Stanfield, S., Corbin, D., and Helinski, D. R., *Proc. Natl. Acad. Sci. USA*, 77, 7347 (1980)) was similarly inoculated to LB medium containing 50 μg/L of kanamycin, which was contained in a 30-ml volume test tube, and cultured at 37° C. for 18 hours with shaking. Further, a wild type strain of *Methylococcus capsulatus* Bath was inoculated to 3 ml of NMS medium contained in a 30-ml volume test tube, in which 15 ml of methane was then enclosed, and cultured at 37° C. for 24 hours with shaking.

Each of cultures of JM109/pCABD2 and HB101/pRK2013 (0.5 ml) was washed twice with 50 mM phosphate buffer (pH 7.0) and suspended in 0.5 ml of the same buffer. 1.3 ml of the culture of the wild type strain of *Methylococcus capsulatus* Bath was mixed with 0.1 ml of the cell suspension of JM109/pCABD2 and 0.1 ml of the cell suspension of HB101/pRK2013, and centrifuged to remove the supernatant.

The obtained cells were mixed with 10 μl of NMS medium, then transferred on an NMS plate, and cultured at 37° C. in the presence of 50% methane. The cells were collected from the plate 48 hours later, then inoculated on an NMS plate containing 10 μg/ml of streptomycin, and cultured at 37° C. for 1 month in the presence of 50% methane.

The emerged colonies were inoculated on an NMS plate containing 10 μg/ml of streptomycin, and cultured at 37° C. for 6 days in the presence of 50% methane. The cells were inoculated into 3 ml of NMS medium containing 10 μg/ml of streptomycin in a 30-ml volume test tube, in which 15 ml of methane was then enclosed, and cultured at 37° C. for 41 hours with shaking.

After the culture was completed, the cells were separated from the culture by centrifugation, and the presence of each plasmid was confirmed in a conventional manner. Hereafter, *Methylococcus capsulatus* Bath strain which harbors pCABD2 is referred to as *Methylococcus capsulatus* Bath/pCABD2.

Example 13

Effect of Amplification of dapA*, lysC*, dapB and ddh Genes in *Methylococcus capsulatus* Bath

*Methylococcus capsulatus* Bath/pRS (comprising only the vector), *Methylococcus capsulatus* Bath/RSF24P (comprising dapA*) and *Methylococcus capsulatus* Bath/pCABD2 (comprising dapA*, lysC*, dapB and ddh) were each inoculated into 3 ml of NMS medium contained in a 30-ml volume test tube, in which 15 ml of methane was then enclosed, and cultured at 37° C. for 65 hours with shaking. As for the strains harboring the plasmids, NMS medium containing 10 μg/ml of streptomycin was used instead of NMS medium. Twenty-two hours and 42 hours after the culture was started, the gaseous phase in the test tube was replaced with air, and 15 ml of methane was newly enclosed. Amino acids contained in the culture supernatant after the culture were quantified in the same manner as in Example 3.

The results are shown in Table 9. The dapA*, lysC*, dapB, and ddh amplified strain (*Methylococcus capsulatus* Bath/pCABD2) accumulated about twice as much L-lysine as the strain in which only dapA* was amplified (*Methylococcus capsulatus* Bath/RSF24P).

TABLE 9

Effect of amplification of dapA*, lysC*, dapB
and ddh in *Methylococcus capsulatus* Bath

| Strain | L-Lys accumulation (mg/L) |
|---|---|
| *Methylococcus capsulatus* Bath/pRS | 0.75 |
| *Methylococcus capsulatus* Bath/RSF24P | 4.32 |
| *Methylococcus capsulatus* Bath/pCABD2 | 9.37 |

What is claimed is:

1. A method for production of an L-amino acid, comprising:
   a) cultivating a L-amino acid producing methane-utilizing microorganism in a culture medium, and wherein said microorganism is in contact with gas containing methane which is the main source of carbon, and wherein said microorganism is selected from the group consisting of *Methylomonas albus, Methylococcus capsulatus,* and *Methylosinus trichosporiurn,* and
   b) collecting said L-amino acid from said medium.

2. A method according to claim 1, wherein said L-amino acid is selected from the group consisting of L-aspartic acid, L-threonine, L-serine, L-glutamic acid, L-proline, L-glycine, L-alanine, L-cysteine, L-valine, L-methionine, L-isoleucine, L-leucine, L-tyrosine, L-phenylalanine, L-lysine, L-histidine, L-arginine and L-tryptophan.

3. A method according to claim 1, wherein said methane-utilizing microorganism is a wild-type strain.

4. A method according to claim 1, wherein said methane-utilizing microorganism is resistant to an L-amino acid or an analog thereof.

5. A method according to claim 4, wherein the L-amino acid is L-lysine and the analog thereof is S-(2-aminoethyl)-cysteine.

6. A method according to claim 1, wherein said methane-utilizing microorganism is a mutant strain in which the activity of at least one enzyme involved in biosynthesis of an L-amino acid is enhanced.

7. A method according to claim 6, wherein the microorganism si a transformed with a vector which encodes at least one enzyme involved in biosynthesis of an L-amino acid.

8. A method according to claim 6 or 7, wherein said enzyme is selected from the group consisting of mutant dihydrodipicolinate synthase which is desensitized to feedback inhibition by L-lysine, mutant aspartokinase which is desensitized to feedback inhibition by L-lysine, dihydrodipicolinate reductase, diaminopimelate dehydrogenase, and conbinations thereof.

* * * * *

SEQUENCE LISTING

<160> NUMBER OF SEQ ID NOS: 5

<210> SEQ ID NO 1
<211> LENGTH: 1197
<212> TYPE: DNA
<213> ORGANISM: Escherichia coli
<220> FEATURE:
<221> NAME/KEY: CDS
<222> LOCATION: (272)..(1147)
<223> OTHER INFORMATION:

<400> SEQUENCE: 1

```
ccaggcgact gtcttcaata ttacagccgc aactactgac atgacgggtg atggtgttca      60
caattccacg gcgatcggca cccaacgcag tgatcaccag ataatgtgtt gcgatgacag     120
tgtcaaactg gttattcctt taaggggtga gttgttctta aggaaagcat aaaaaaaaca     180
tgcatacaac aatcagaacg ttctgtctg cttgctttta atgccatacc aaacgtacca     240
ttgagacact tgtttgcaca gaggatggcc c atg ttc acg gga agt att gtc        292
                                   Met Phe Thr Gly Ser Ile Val
                                    1               5 gcg att gtt act ccg atg gat gaa aaa ggt aat gtc tgt cgg gct agc       340
Ala Ile Val Thr Pro Met Asp Glu Lys Gly Asn Val Cys Arg Ala Ser
            10                  15                  20 ttg aaa aaa ctg att gat tat cat gtc gcc agc ggt act tcg gcg atc       388
Leu Lys Lys Leu Ile Asp Tyr His Val Ala Ser Gly Thr Ser Ala Ile
     25                  30                  35 gtt tct gtt ggc acc act ggc gag tcc gct acc tta aat cat gac gaa       436
Val Ser Val Gly Thr Thr Gly Glu Ser Ala Thr Leu Asn His Asp Glu
40                  45                  50                  55 cat gct gat gtg gtg atg atg acg ctg gat ctg gct gat ggg cgc att       484
His Ala Asp Val Val Met Met Thr Leu Asp Leu Ala Asp Gly Arg Ile
                60                  65                  70 ccg gta att gcc ggg acc ggc gct aac gct act gcg gaa gcc att agc       532
Pro Val Ile Ala Gly Thr Gly Ala Asn Ala Thr Ala Glu Ala Ile Ser
        75                  80                  85 ctg acg cag cgc ttc aat gac agt ggt atc gtc ggc tgc ctg acg gta       580
Leu Thr Gln Arg Phe Asn Asp Ser Gly Ile Val Gly Cys Leu Thr Val
    90                  95                 100 acc cct tac tac aat cgt ccg tcg caa gaa ggt ttg tat cag cat ttc       628
Thr Pro Tyr Tyr Asn Arg Pro Ser Gln Glu Gly Leu Tyr Gln His Phe
105                 110                 115 aaa gcc atc gct gag cat act gac ctg ccg caa att ctg tat aat gtg       676
Lys Ala Ile Ala Glu His Thr Asp Leu Pro Gln Ile Leu Tyr Asn Val
120                 125                 130                 135 ccg tcc cgt act ggc tgc gat ctg ctc ccg gaa acg gtg ggc cgt ctg       724
Pro Ser Arg Thr Gly Cys Asp Leu Leu Pro Glu Thr Val Gly Arg Leu
                140                 145                 150 gcg aaa gta aaa aat att atc gga atc aaa gag gca aca ggg aac tta       772
Ala Lys Val Lys Asn Ile Ile Gly Ile Lys Glu Ala Thr Gly Asn Leu
            155                 160                 165 acg cgt gta aac cag atc aaa gag ctg gtt tca gat gat ttt gtt ctg       820
Thr Arg Val Asn Gln Ile Lys Glu Leu Val Ser Asp Asp Phe Val Leu
        170                 175                 180 ctg agc ggc gat gat gcg agc gcg ctg gac ttc atg caa ttg ggc ggt       868
Leu Ser Gly Asp Asp Ala Ser Ala Leu Asp Phe Met Gln Leu Gly Gly
    185                 190                 195 cat ggg gtt att tcc gtt acg act aac gtc gca gcg cgt gat atg gcc       916
His Gly Val Ile Ser Val Thr Thr Asn Val Ala Ala Arg Asp Met Ala
200                 205                 210                 215
```

```
cag atg tgc aaa ctg gca gca gaa gaa cat ttt gcc gag gca cgc gtt      964
Gln Met Cys Lys Leu Ala Ala Glu Glu His Phe Ala Glu Ala Arg Val
        220                 225                 230 att aat cag cgt ctg atg cca tta cac aac aaa cta ttt gtc gaa ccc     1012
Ile Asn Gln Arg Leu Met Pro Leu His Asn Lys Leu Phe Val Glu Pro
            235                 240                 245 aat cca atc ccg gtg aaa tgg gca tgt aag gaa ctg ggt ctt gtg gcg     1060
Asn Pro Ile Pro Val Lys Trp Ala Cys Lys Glu Leu Gly Leu Val Ala
        250                 255                 260 acc gat acg ctg cgc ctg cca atg aca cca atc acc gac agt ggt cgt     1108
Thr Asp Thr Leu Arg Leu Pro Met Thr Pro Ile Thr Asp Ser Gly Arg
        265                 270                 275 gag acg gtc aga gcg gcg ctt aag cat gcc ggt ttg ctg taaagtttag      1157
Glu Thr Val Arg Ala Ala Leu Lys His Ala Gly Leu Leu
280                 285                 290 ggagatttga tggcttactc tgttcaaaag tcgcgcctgg                         1197

<210> SEQ ID NO 2
<211> LENGTH: 292
<212> TYPE: PRT
<213> ORGANISM: Escherichia coli

<400> SEQUENCE: 2

Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
            20                  25                  30

Ala Ser Gly Thr Ser Ala Ile Val Ser Val Gly Thr Thr Gly Glu Ser
        35                  40                  45

Ala Thr Leu Asn His Asp Glu His Ala Asp Val Val Met Met Thr Leu
    50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
        195                 200                 205

Val Ala Ala Arg Asp Met Ala Gln Met Cys Lys Leu Ala Ala Glu Glu
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255
```

-continued

```
Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
        290

<210> SEQ ID NO 3
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
gcgcgaattc caacgggcaa tatgtctctg                                     30

<210> SEQ ID NO 4
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
gcgccaattg gatgtaccgc cgaacttcaa                                     30

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
cagttttctg atgaagcgcg                                                20
```